United States Patent [19]
Stevens

[11] Patent Number: 5,892,570
[45] Date of Patent: Apr. 6, 1999

[54] METHOD AND APPARATUS FOR MEASURING AND CORRECTING METAMORPHOPSIA

[75] Inventor: Kent A. Stevens, Eugene, Oreg.

[73] Assignee: State of Oregon Acting by and through the State Board of Higher Education on Behalf of the University of Oregon, Eugene, Oreg.

[21] Appl. No.: 977,186

[22] Filed: Nov. 24, 1997

[51] Int. Cl.$^6$ ........................................................ A61B 3/02
[52] U.S. Cl. ............................ 351/237; 351/222; 351/246
[58] Field of Search ...................................... 351/222, 223, 351/224, 225, 226, 243, 246, 200, 237, 238, 239, 240, 241, 242

[56] References Cited

U.S. PATENT DOCUMENTS

| | | |
|---|---|---|
| 3,025,755 | 3/1962 | Koetting . |
| 3,837,734 | 9/1974 | Regan . |
| 4,511,228 | 4/1985 | Von Gierke et al. ................... 351/243 |
| 4,798,456 | 1/1989 | Enoch et al. . |
| 5,231,673 | 7/1993 | Elenga . |
| 5,308,991 | 5/1994 | Kaplan . |

Primary Examiner—Hung Xuan Dang
Attorney, Agent, or Firm—Klarquist Sparkman Campbell Leigh Whinston, LLP

[57] ABSTRACT

A method and apparatus are provided for the evaluation and measurement of metamorphopsia. The apparatus includes a pattern generator that displays a deformable pattern, such as an Amsler grid, on a computer monitor. The rectilinear grid includes substantially parallel and equally spaced lines that intersect at vertices. An input device, such as a mouse, is used by a patient or technician to detect areas of the pattern where the cursor is not visible to the subject, so that areas of scotoma can be marked. The input device is also used to adjust the positions of the vertices, and distort the grid, until the grid appears substantially rectilinear to the subject. The deformations of the pattern are then recorded, and can be retrieved for comparison to subsequent test results so that changes in visual field deficits or metamorphopsia can be sensitively detected, and even corrected by a lens that distorts images in the same pattern. The present invention provides a very sensitive test for metamorphopsia that detects early retinal changes at a time when therapeutic intervention may be more helpful. The test can also be conveniently used at home, for example on a personal computer, so that the subject can be tested frequently and easily. The results of the test are mathematical maps or functions (image distortion as a function of image location) that can be used to provide therapeutic correction of metamorphopsia.

28 Claims, 6 Drawing Sheets

METHOD AND APPARATUS FOR MEASURING AND CORRECTING METAMORPHOPSIA

FIELD OF THE INVENTION

The invention pertains to a method and apparatus for diagnosing, quantitating, recording and correcting metamorphopsia.

BACKGROUND OF THE INVENTION

Metamorphopsia is a geometric distortion of the visual field which is often associated with retinal (particularly macular) disorders such as age-related macular degeneration (ARMD) and retinal detachments. This disorder causes a patient's visual space to appear warped, as if looking through rippled glass. A patient with metamorphopsia often complains that edges that should be straight (such as the edge of a door or window) instead appear bent in the affected regions of the visual field. This distortion can lead to severe visual impairment.

ARMD is the leading cause of severe visual loss among older adults in the Western world, and this disease is one of the most common causes of metamorphopsia. ARMD is characterized by the development of pigmentary changes, neovascularization, hemorrhages and edema in the macula, which is the region of greatest retinal sensitivity. These changes gradually destroy the sensitivity of portions of the macula, and can lead to the loss of central, high acuity vision. If some of these pathological changes are detected in early stages, laser photocoagulation of neovascular nets can slow or prevent the development of advanced disease. The detection of early metamorphopsia is therefore an important tool in the early diagnosis and treatment of this sight threatening condition.

A common clinical approach for detecting metamorphopsia is to use the Amsler grid, which is a printed square grid, usually 10 cm wide and 10 cm high, containing equally spaced, parallel horizontal and vertical lines. Typical embodiments of the printed grid include individual 5 mm×5 mm squares of equal area, arranged around a fixation point (such as a dot) at the center of the grid. In use, the grid is held at arm's length, e.g. a distance of about 28–30 cm, while one eye is occluded, and the open eye fixes on the central fixation point. Areas of distortion or wavy lines are then noted by the subject, who may draw a circle around the areas of grid distortion. The subject is also asked to report any changes in the severity or distribution of the distortion, which can indicate progress of the retinal pathology that requires immediate treatment.

One problem with the Amsler Grid, however, is that it provides a poor record of the metamorphopsia, which can only be grossly recorded by pointing to the distortion or drawing a line around it. Detection of the progression of the metamorphopsia is often missed because of the inability to accurately record or recall earlier distortion patterns. In addition, subtle changes in the metamorphopsia are often missed altogether, or not detected until irreversible macular damage has occurred.

Although detection of the distortion, and changes in the distortion, are important for diagnosis, there is also a need to rehabilitate persons who are visually impaired by severe metamorphopsia. Optical correction of metamorphopsia has not been a clinical option in the past, however, because of the inability to accurately measure metamorphopsia in a manner that would permit optical correction. It has also been uncertain that metamorphopsic distortion could be corrected or optically compensated, because visual disturbances sometimes cause further neurophysiologic changes (as in amblyopia) that affect mapping of the visual space within the primary visual cortex, and elsewhere in the visual pathways. If such changes in the central nervous system occurred with metamorphopsia, it would interfere with the ability to correct the distortion for purposes of either diagnosis or treatment.

U.S. Pat. No. 4,798,456 disclosed a hyperacuity method for evaluating metamorphopsia in which at least two fixed spots are displayed on a screen, and a subject moves a mobile spot on the screen to align the mobile spot with the fixed spots. The difference between the actual point of alignment and the perceived point of alignment is an indication of the metamorphopsia present at a particular location in the visual field. However this technique only measures distortion that corresponds to a particular point on the retina, and it lacks the ability of the Amsler grid to globally analyze visual perception across the central visual field. The disclosed hyperacuity method also suffers from the inability to allow the subject to compare the equal areas of adjacent squares in the grid, which provide valuable perceptual information that assists in the detection and quantitation of metamorphopsia.

Another retinal problem that often accompanies retinal disease is the development of a scotoma, or a blind spot in the visual field. A scotoma may either be absolute (no vision in the area of the visual deficit) or relative (poor light perception in the area of the visual deficit). A scotoma can be detected on an Amsler grid as an area of missing squares in the regular grid pattern. The presence of the scotoma may also provide additional important diagnostic information, particularly if the scotoma has enlarged or otherwise changed. Visual field deficits are usually measured and recorded in perimetry devices (such as a Goldmann Perimeter).

It is an object of this invention to provide a precise and sensitive device for detecting and recording visual distortion caused by metamorphopsia.

Another object of the invention is to provide such a device which can also detect and record visual field deficits, such as a scotoma.

Yet another object is to provide such as device that can easily be used at home by a subject for frequent testing.

Yet another object is to quantitate visual distortion caused by metamorphopsia, so that subtle changes in distortion can be detected.

Even yet another object is to quantitate the distortion so that the distortion can be optically corrected.

SUMMARY OF THE INVENTION

The foregoing objects are achieved by the present invention, which is an apparatus for accurately detecting, quantitating, and storing patterns of visual distortion caused by metamorphopsia in a subject. The apparatus includes a display (such as a computer screen) that displays a regular pattern (such as a grid) suitable for detecting metamorphopsia as a distortion of the pattern. An input device allows the subject to selectively deform the pattern until the distortion of metamorphopsia is geometrically neutralized, and the pattern appears substantially regular. A recorder (such as computer memory or a printer) then records the pattern of distortion that neutralizes the metamorphopsia, so that the pattern can be compared to future tests to detect changes. Subtle changes in the pattern can be noted by the subject or a technician, so that the subject can immediately seek a retinal examination and treatment (such as laser photocoagulation of neovascular nets). A stable pattern of distortion can also be used to make a corrective lens or other filter that can optically correct the metamorphopsia, and improve the visual function of the subject.

The apparatus is also capable of measuring a visual field deficit, such as a scotoma. A cursor can be moved throughout the pattern, and a marker placed in areas of the pattern where the cursor is not perceived by the subject. The marked areas can then be noted (and printed or digitally stored) for future comparison. The marked areas not only measure visual field deficits, but also help prevent misregistration of visual fixation during subsequent metamorphopsia testing. If the subject's visual fixation wanders from a preselected target, the markers in the areas of scotoma will become visible, which will alert the subject to return gaze to the fixation target.

The pattern may be generated by a pattern generator associated with a computer, such as a personal computer. Disclosed embodiments of the pattern are regular, contain equally spaced, orthogonal lines, and define multiple patterns of equal geometric areas that appear unequal if metamorphopsia is present. The lines of the pattern intersect at vertices, which can be moved along the intersecting lines to distort the pattern and neutralize the perception of metamorphopsia.

The invention also includes a method of evaluating or treating metamorphopsia, in which the regular pattern is displayed to the subject, who selectively deforms the pattern by moving the vertices along the intersecting lines. Visual field deficits are also marked on the pattern by moving a cursor throughout the pattern and marking areas of the pattern where the cursor is not perceived by the subject.

The invention also includes a computer system for displaying the pattern, and allowing the subject to mark areas of scotoma and metamorphopsia. The computer system also records the areas of scotoma and visual distortion, and can be programmed to automatically note any significant changes in the results that may indicate a progression of disease that requires medical attention. The computer system can also calculate optical corrections that are needed to neutralize the distortion perceived by the subject.

The method further comprises measuring visual sensitivity to misregistration of the deformed (i.e., corrected) pattern. Misregistration sensitivity may be determined by smooth visual pursuit of a cursor as it moves away from a point of registration (such as the central target), or by incrementally shifting the fixation point until distortion becomes apparent to the subject. The displacement (in millimeters or degrees of visual arc) at which distortion becomes apparent to the subject is the misregistration threshold. Subjects who are very sensitive to misregistration may experience more difficulty with optical correction of metamorphopsia.

The apparatus and method of the present invention are easily used in either a clinical setting or at home. It is particularly advantageous for home use, because it can be installed on a home computer and used frequently by the subject to detect changes in visual distortion (metamorphopsia) or visual field defects (scotoma) that indicate the need for urgent ophthalmic evaluation and treatment.

The foregoing and other features and advantages of the invention will become more apparent from the following detailed description of several preferred embodiments which proceed with reference to the accompanying drawings.

DETAILED DESCRIPTION OF SEVERAL EMBODIMENTS

Computer System

Figure 1:
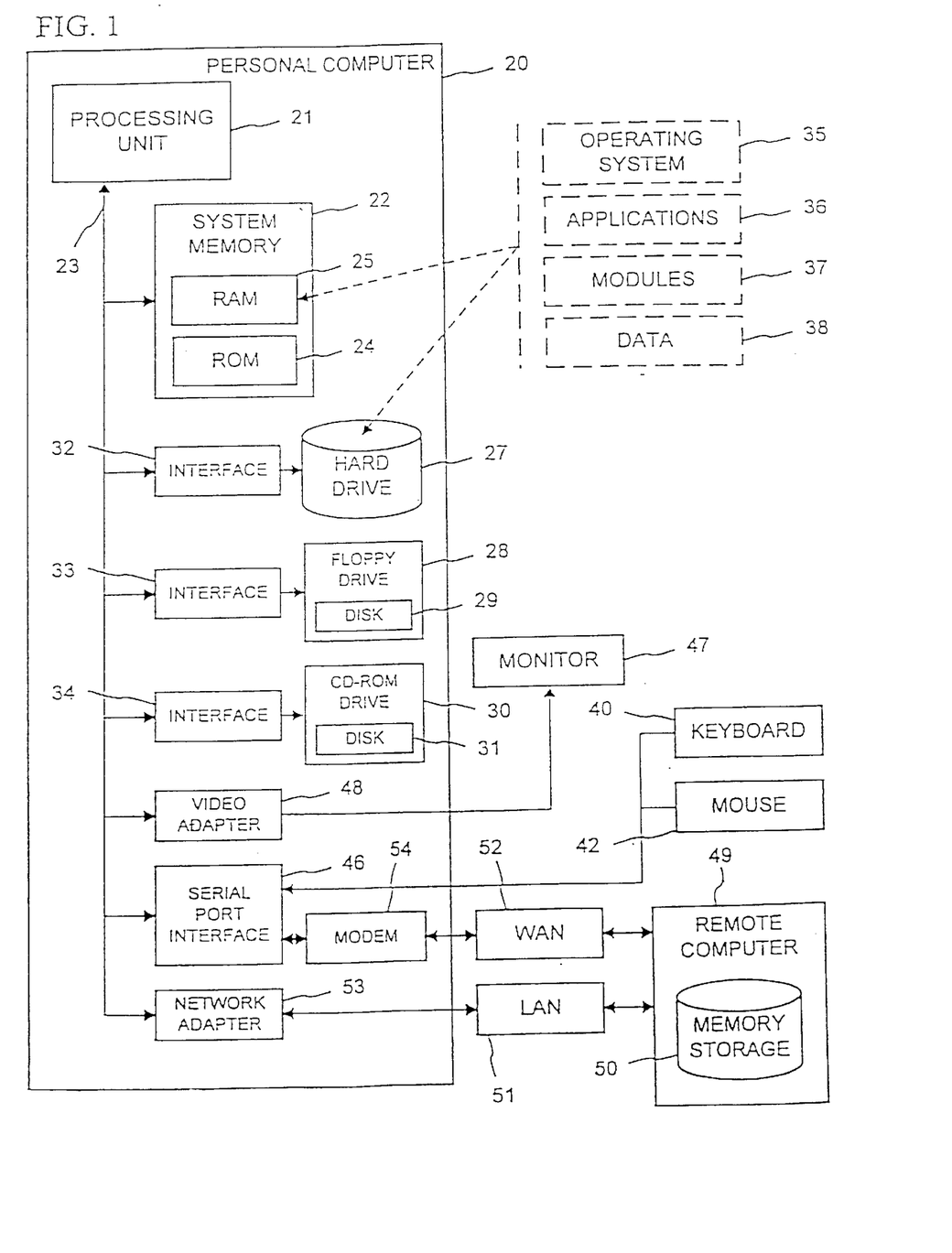
FIG. 1 is a schematic drawing illustrating a computer system in which the invention can be implemented.

FIG. 1 and the following discussion are intended to provide a brief, general description of a specific example of a suitable environment in which the invention may be implemented. While the invention will be described in the general context of computer-executable instructions of a computer program that runs on a personal computer, those skilled in the art will recognize that the invention also may be implemented without a computer, or in combination with other program modules. Generally, program modules include routines, programs, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like.

The invention may also be practiced in distributed computing environments where tasks are performed by remote processing devices that are linked through a communications network. In a distributed computing environment, program modules may be located in both local and remote memory storage devices. Moreover, the invention is need not be used with a computer at all, but may also be implemented with any digital or analog system, or future variations of present computer systems. The implementation of the mapping technique does not rely on any computer system as currently practiced. The invention may also be used in association with mechanical, video, electromechanical, optical, or electro-optical techniques.

With reference to FIG. 1, an exemplary system for implementing the invention in one specific computer environment includes a conventional personal computer 20, including a processing unit 21, a system memory 22, and a system bus that couples various system components including the system memory to the processing unit 21. The system bus may be any of several types of bus structure including a memory bus or memory controller, a peripheral bus, and a local bus using any of a variety of conventional bus architectures such as PCI, VESA, Microchannel, ISA and EISA, to name a few.

The system memory includes a read only memory (ROM) 24 and random access memory (RAM) 25. A basic input/output system 26 (BIOS), containing the basic routines that helps to transfer information between elements within the personal computer 20, such as during start-up, is stored in ROM 24.

The personal computer 20 further includes a hard disk drive 27, a magnetic disk drive 28, e.g., to read from or write to a removable disk 29, and an optical disk drive 30, e.g., for reading a CD-ROM disk 31 or to read from or write to other optical media. The hard disk drive 27, magnetic disk drive 28, and optical disk drive 30 are connected to the system bus 23 by a hard disk drive interface 32, a magnetic disk drive interface 33, and an optical drive interface 34, respectively. The drives and their associated computer-readable media provide nonvolatile storage of data, data structure, computer-executable instructions, and the like for the personal computer 20. Although the description of computer-readable media above refers to a hard disk, a removable magnetic disk and a CD, it should be appreciated by those skilled in the art that other types of media which are readable by computer, such as magnetic cassettes, flash memory card, digital video disks, Bernoulli cartridges, and the like, may also be used in the exemplary operating environment.

A number of program modules may be stored in the drive's RAM 25, including an operating system 35, one or more application programs 36, other program modules 37, and program data 38. A user may enter commands and information into the personal computer 20 through a keyboard 40 and a pointing device, such as a mouse 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB). A monitor 47 or other type of display device is also connected to the system bus 23 via an interface, such as a video adapter 48. In addition to the monitor, personal computers typically include other peripheral output devices (not shown), such as speakers and printers.

The personal computer 20 may operate in a networked environment using logical connections to one or more remote computers, such as a remote computer 49. The remote computer 49 may be a server, a router, a peer device or other common network node, and typically includes many or all of the elements described relative to the personal computer 20, although only a memory storage device 50 has been illustrated in FIG. 1. The logical connections depicted in FIG. 1 include a local area network (LAN) 51 and a wide area network (WAN) 52. Such networking environments are commonplace in offices, enterprise-wide computer networks (such as hospital computers), intranets and the Internet.

When used in a LAN networking environment, the personal computer 20 is connected to the local network 51 through a network interface or adapter 53. When used in a WAN networking environment, the personal computer 20 typically includes a modem 54 or other means for establishing communications over the wide area network 52, such as the Internet. The modem 54, which may be internal or external, is connected to the system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

The present system is implemented in C ++ on an SGI computer, but it can similarly be implemented on an IBM compatible or Macintosh computer, for example on an IBM compatible personal computer having at least eight megabytes of main memory and a gigabyte hard disk drive, with Microsoft Windows as the user interface.

Computer Implemented Embodiment

Figures 2A, 2B:
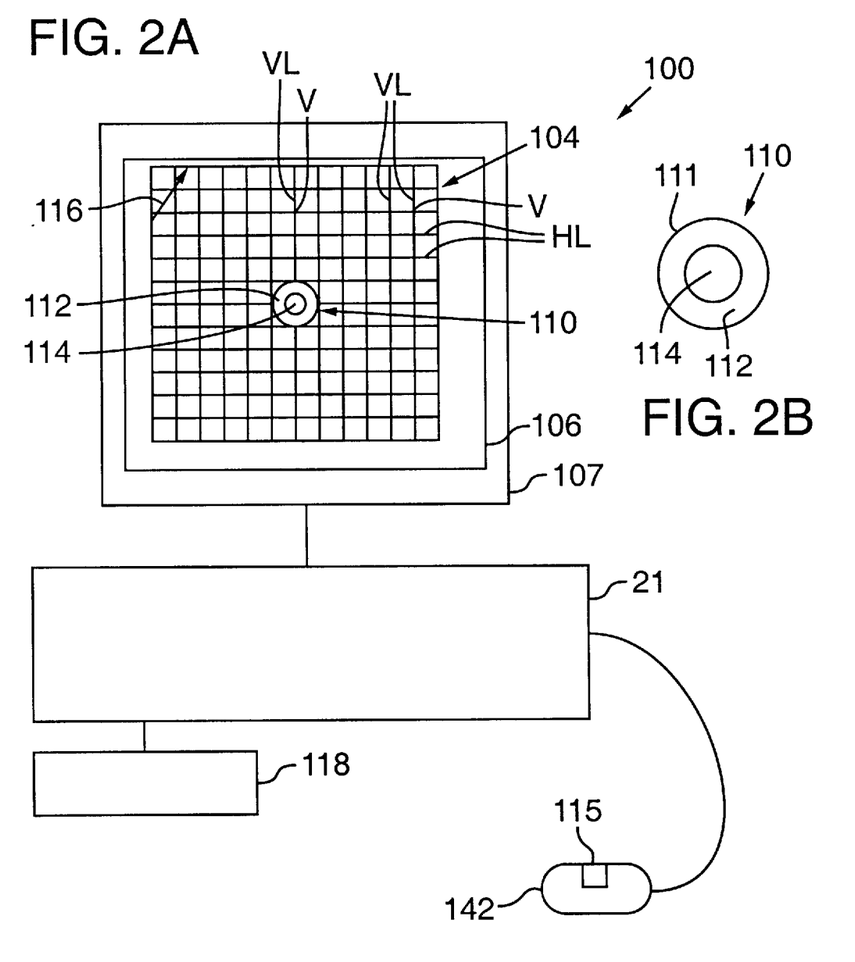
FIGS. 2A and 2B are a schematic views of an apparatus for measuring metamorphopsia using a deformable grid pattern shown on the screen.

With reference to FIG. 2, an apparatus 100 for measuring metamorphopsia comprises a pattern generator in the CPU 21 that generates a deformable Amsler grid 104 or other deformable pattern. The Amsler grid is the standard means for diagnosing and measuring metamorphopsia, and will therefore be shown as the preferred embodiment. The Amsler grid pattern includes horizontal and vertical lines, at right angles to each other, that are globally straight over a reasonable portion of the central visual field when held at a comfortable viewing distance. The intersecting lines form a pattern of squares of equal area to be viewed by the subject.

The deformable grid pattern 104 is displayed on a display screen 106 of a standard computer monitor 47 (FIG. 1) placed a suitable distance from the subject. typically a distance of 0.3 to 1 meter. The distance between the screen and the subject is typically sufficient that the individual squares of the box subtend an angle of about 1° of visual field at the selected distance. The individual squares with equal length sides, and adjacent squares with equal areas, provide regular patterns that are interrupted in a subject experiencing metamorphopsia. Such a subject will see the grid as distorted, with distortions that shift as the eye traverses the grid. Visual fixation may be fixed, for example in the center of the grid, to stabilize the pattern of distortion, and provide a basis for comparison with prior and subsequent tests.

A fixation target 110 is displayed at the center of the grid pattern 104 in FIG. 2, and is in the form of a white circular ring 112 surrounding a red circle 114. In the preferred embodiment, the display screen 106 of the computer monitor 47 has 38.86 pixels/cm, and the deformable grid pattern 104 is 800 pixels by 800 pixels or 20.59 cm by 20.59 cm. The lines of the grid are equally spaced at 50 pixels, or about 1.29 cm. The fixation target 110 is 10 pixels or 2.6 mm in diameter. In addition to the fixation target 110 and the deformable pattern 104, a small red arrow 116 serves as a cursor that can be moved throughout the pattern 104. A red dot or other marker (such as an X) may be placed on the pattern at the position of the cursor arrow 116 by clicking the mouse 42, for example by depressing an actuator 115.

Grid pattern 104 includes a plurality of orthogonal horizontal lines HL and vertical lines VL that intersect at vertices V. In the disclosed embodiment, the computer 20 is programmed to interact with the mouse 42 to deform the pattern. In particular, the mouse is used to position the cursor 116 pointing at a vertex V, and to reposition the vertex along a horizontal line HL, a vertical line VL, or both. In this manner each square of the grid pattern 104 can be changed to a trapezoid that approximates a curvature that is geometrically equal and opposite to the distortion seen by the subject. It has surprisingly been found that such a geometrically opposite pattern can neutralize the optical distortion seen by the subject who is experiencing metamorphopsia.

The geometrically opposite pattern is, mathematically, a function that maps an ideal image into a distorted image. The function is one-to-one, spatially continuous and time invariant (at least approximately so in subjects who do not have progressive retinal disease), hence performing an optical correction by distorting the pattern is conceivable. However, visual perception involves subjective cortical experience, and many perceptual functions cannot be fully compensated for once they are disturbed. Thus while the geometric distortion has an optical inverse, it was not previously known that the distortion had a neuropsychological inverse. The following examples illustrate the encouraging finding that the visual distortion can be canceled by a pattern distorted to neutralize metamorphopsia.

The mouse 42 is programmed to communicate with the pattern generator 103 to provide input used to distort the deformable Amsler grid pattern 104. The distortion can be accomplished, for example, by pointing the cursor to a vertex V, depressing the mouse button 114 and maintaining the button 114 depressed while dragging the vertex V to a desired position, then releasing pressure on the button 114. Upon receiving input from the mouse 42, the pattern generator of the computer program makes a corresponding change in the deformable grid pattern 104. A recorder 118, such as a CD ROM or disk drive, is also provided for recording and storing the deformations of the deformable grid pattern 104. The deformations may be recorded as two spatially continuous scalar fields, one giving the magnitude of displacement horizontally at each point in the image, and the other giving the magnitude of vertical displacement, relative to an unaffected visual image. Those functions would be constant and zero for an ideal normal subject.

Since the geometric distortion associated with metamorphopsia is continuous and smoothly varying, the grid pattern provides a tool to sample the visual field at a square grid of image locations, as long as visual fixation is held at the center of the grid. If, for example, a given grid line at a grid location appeared bowed to the subject, then bending the line of the display downward has now been found by the inventor to produce an impression of straightness to the subject. Each horizontal line can be deformed by adjusting the vertical position of each vertex along its length, and each vertical line can be deformed by displacing each vertex horizontally. The resulting grid becomes a mesh of trapezoids, but for small grid spacing the displaced lines appear approximately smoothly curved. In this manner the apparatus 100 can be used to measure the net effective distortion across the subject's visual field using the interactive software system.

Although the overall appearance of the grid distortion is typically used to screen for the presence of macular changes that may indicate progression of retinal disease, the distortions can also be quantitated to provide a numerical indication of disease. The difference between the normal, undistorted area of each square and the distorted area of each square can, for example, be summed or averaged to note changes between test sessions.

Use of the invention to detect changes in metamorphopsia, and to detect areas of scotoma, are illustrated in the following Examples.

EXAMPLE 1

A subject is seated in front of a monitor 100, facing pattern 104 on the display screen, at a distance of about 33 cm. One eye is covered by an occluder or patch, and room illumination is controlled to provide a display that is substantially free of reflections. The grid pattern 104 is formed by white line against a black background.

If the subject is known to have a scotoma, the grid is used to map the spatial extent of the scotoma. The scotomata were mapped by asking the subject to establish visual fixation (which was usually foveal fixation) on the target 110, while the cursor 116 was moved over the grid image either by the subject or a technician (who could be, for example, a researcher, physician, optician, nurse or ophthalmic assistant). When the subject notes that the cursor is no longer visible, a small red disk is added to the image, one disk each time the mouse button 114 is depressed. The disks are completely invisible when they fall entirely within the margins of the scotoma. If the subject notes a faint pink spot, particularly along the margin of the scotoma, some or all of the red pixels in that vicinity can be removed. The red pixels can be removed, for example, by using the mouse to paint black disks over the red pixels. By further refinement of adding and obliterating red pixels, the margin of the scotoma becomes apparent as the red spots merge to from a contiguous region.

If the subject loses visual fixation on target 110, the subject will begin to see some of the red margin, which prompts the subject to return to fixation on target 110. Finer precision of scotoma mapping can be accomplished by using progressively smaller spots. Once the area or areas of scotoma are mapped, they also help maintain fixation during subsequent metamorphopsia mapping because the red spots will not be perceived unless the subject loses fixation.

The visual distortion is then mapped by adjusting the vertices V along the horizontal lines HL and vertical lines VL to distort the grid until it appears substantially or precisely rectilinear to the subject, with squares of equal area. In the following Examples 2–4, the subject was first asked to direct attention to any horizontal line that appeared most distorted. The subject could then either use the mouse, or direct a technician to use the mouse, to increase or decrease the horizontal or vertical curvature at any given point by adjusting the position of one or more of the vertices V. Neighboring horizontal lines were addressed similarly, after which attention was directed to vertical lines that appeared particularly distorted, which were similarly corrected by or at the direction of the subject.

Misregistration tolerance is a function of the severity and location of the retinal distortion causing the metamorphopsia. Less severe metamorphopsia (with more gradual and less pronounced distortion) permits greater misregistration tolerance. Misregistration tolerance was tested by asking the subject not to fixate on the target 110, but instead to follow the mouse cursor 116 as it was progressively displaced. While using smooth pursuit eye movements, the subject was asked to notice the quality of the grid as it was progressively brought out of the original distortion-canceling alignment. The subject was asked to report when the grid pattern began to appear distorted, for each of a series of deflections of the point of gaze away from the center of the grid, and when it no longer appeared distorted for a series of returns of visual fixation to the target 110. The midpoint of these two series of observations was considered a threshold tolerance for misregistration.

The process of mapping the scotoma and visual field distortion of the opposite eye was then performed by repeating the above procedure for that eye, with vision of the first tested eye occluded.

The use of the apparatus 100 is further illustrated in the following Examples, which provide case histories of actual uses of the device and method.

EXAMPLE 2

An 83 year old retired male artist presented with advanced ARMD and a paracentral scotoma in the right eye which spared the fovea (the area of the macula with the greatest concentration of photoreceptors, and highest visual acuity). The left eye was patched, the subject was placed approximately 33 cm from the screen, and the right eye was tested as in Example 1 while the subject was wearing his normal corrective spectacles. The grid lines of the pattern 104 were separated horizontally and vertically by 50 pixels, or 2.23 degrees at that viewing distance. The overall pattern image subtended about 35.7 degrees in width and height.

Figure 4:
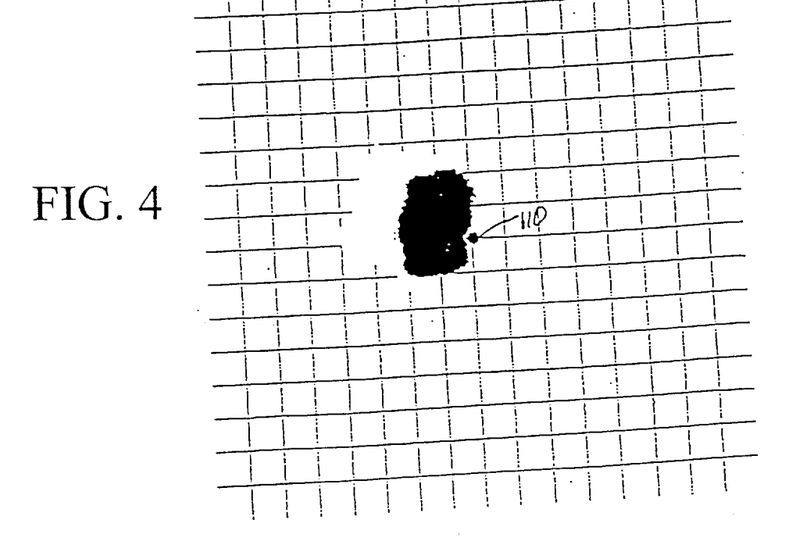
FIGS. 4 and 5 are grid pattern records showing how a scotoma (FIG. 4) and metamorphopsia (FIG. 5) is detected and recorded in a subject using the present invention.
Figure 5:
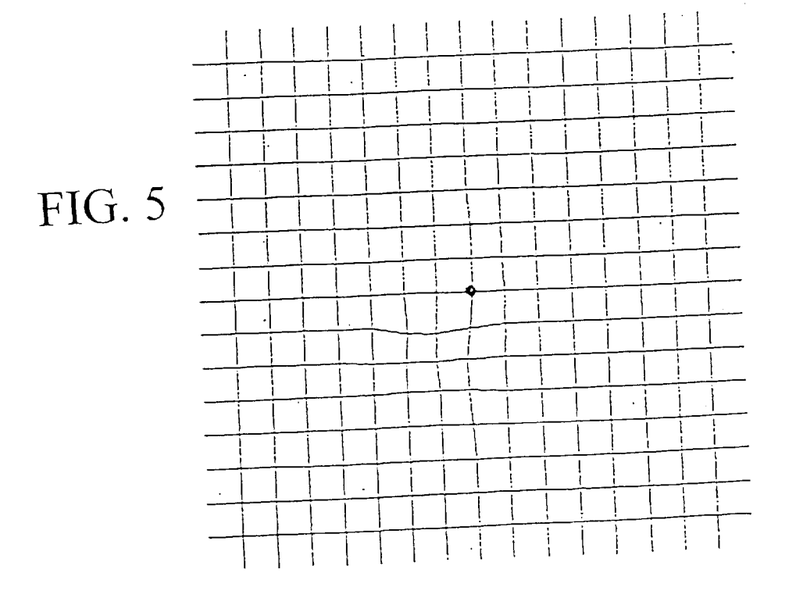

The subject's scotoma was mapped first, with fine precision used along the margins of the field defect, as shown in FIG. 4. After approximately 30 minutes of mapping time, the scotoma was mapped such that the subject saw, at most, a slight pink haze at a few points along the margin of the scotoma when fixating at the central marker 110. Then the subject was presented with the deformable grid pattern, as in Example 1, and the pattern was distorted until it appeared undistorted to the subject. The resulting grid pattern is shown in FIG. 5.

Misregistration tolerance was tested as in Example 1, and the subject found that the map was acceptably rectilinear when misregistered by less than approximately one square width. At the 33 cm viewing distance, that represented about 2 degrees of tolerance to misregistration.

EXAMPLE 3

Figure 6:
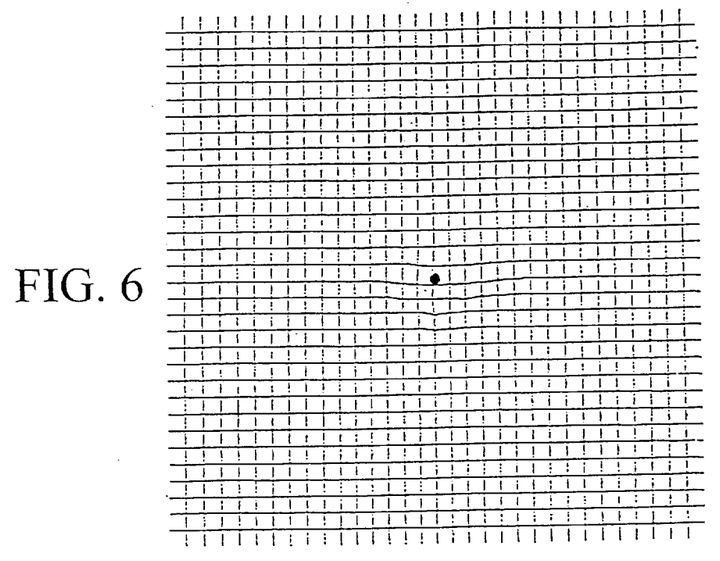
FIG. 6 is a record of a test result in a subject having parafoveal visual field distortion.

An 83 year old male subject with an epiretinal membrane and macular pucker had 20/80 best corrected visual acuity, and no scotoma. This subject viewed the grid pattern at a distance of 63 cm, at which distance a single pixel subtended 1.4 arc minutes, the 25 pixel spacing between grid lines subtended 0.6 arc degrees, and the overall grid subtended about 18.6 degrees. After performing distortion mapping as in Example 1, the distortion pattern shown in FIG. 6 was obtained. This pattern was perceived by the subject as being regular, with each of the small squares substantially rectilinear.

Figure 7:
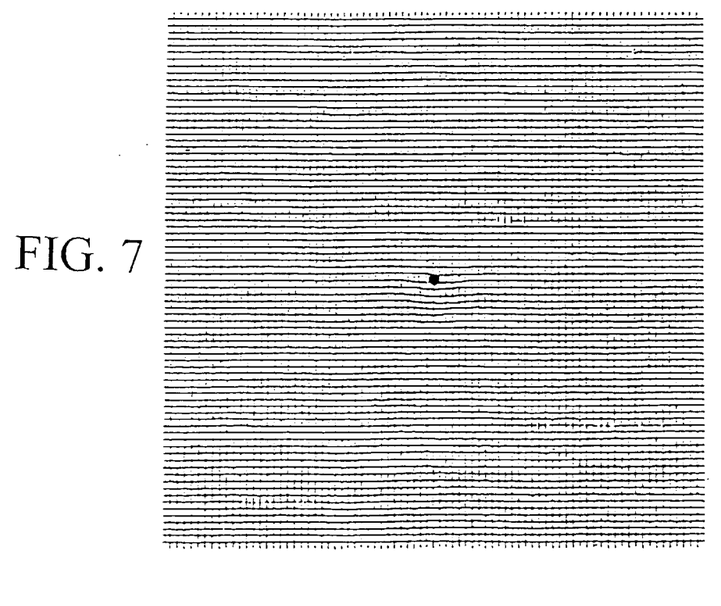
FIG. 7 is a record of a test result from the same subject as shown in FIG. 6, but with a higher resolution in a grid having lines that are more tightly spaced.

A more detailed mapping was then obtained with a finer grid pattern, shown in FIG. 7. The lines were spaced horizontally and vertically by 10 pixels, which placed the lines only 14 arc minutes apart. This pattern was more tedious for the subject to produce.

EXAMPLE 4

A 66 year old female artist presented with marked visual distortion in her right eye, caused by a retinal pigment epithelial detachment in the clinical context of pre-existing ARMD. Her best corrected visual acuity in that eye was 20/60. The right eye was tested first, with a patch over the left eye, and with her corrective eyewear in place. With spectacle correction, she was comfortable viewing the grid pattern at a distance of 63 cm.

Figure 8:
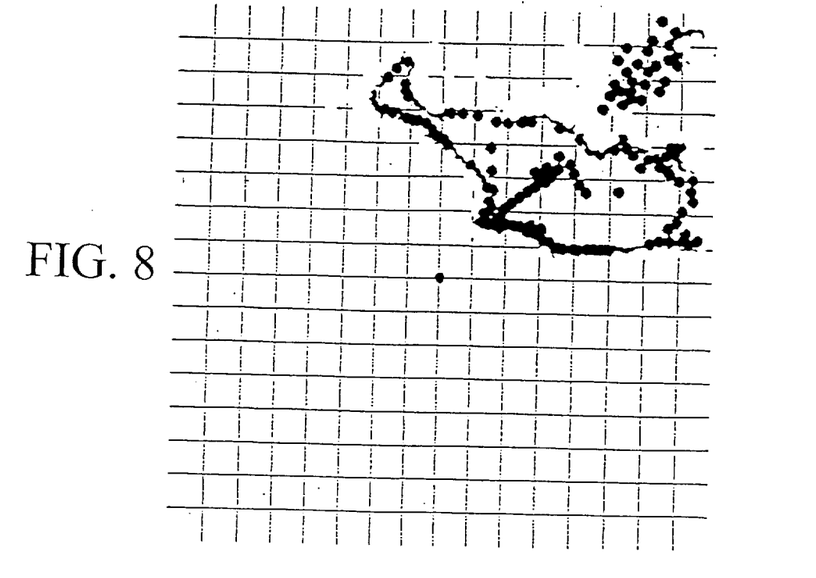
FIG. 8 is a record of a test result from another subject, where a paracentral scotom a has been mapped.
Figure 9:
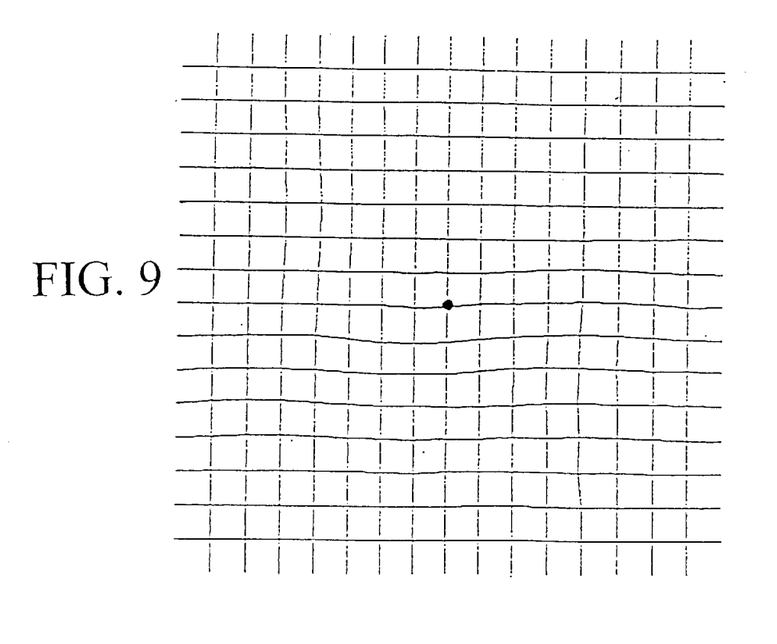
FIG. 9 is a record of visual distortion mapping of the same subject as in FIG. 8.

As shown in FIG. 8, she had an extensive paracentral scotoma, which was mapped coarsely within the right upper quadrant of her visual field. The central portion of the scotoma was mapped carefully, while the more peripheral margin of the scotoma was not mapped. As shown in FIG. 8, the scotoma margin was located by a series of disks that were placed at successively closer locations radially until just visible to the subject. The distortion mapping was then performed by moving the vertices of the affected horizontal and vertical lines of the grid pattern. The result of the distortion mapping is shown in FIG. 9, which represents the pattern that neutralizes the distortion perceived by the subject with metamorphopsia.

EXAMPLE 5

Figure 3A:
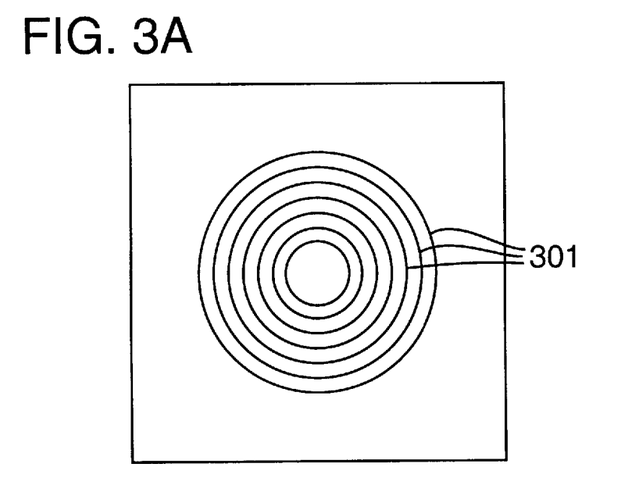
FIGS. 3A, 3B,and 3C are representative deformable patterns suitable for use in the apparatus of FIG. 1
Figure 3B:
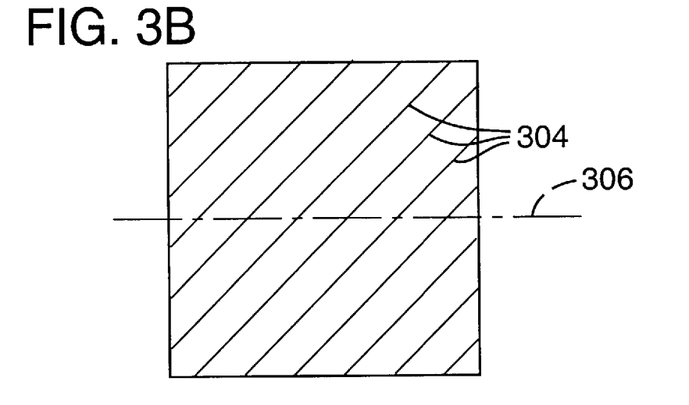
Figure 3C:
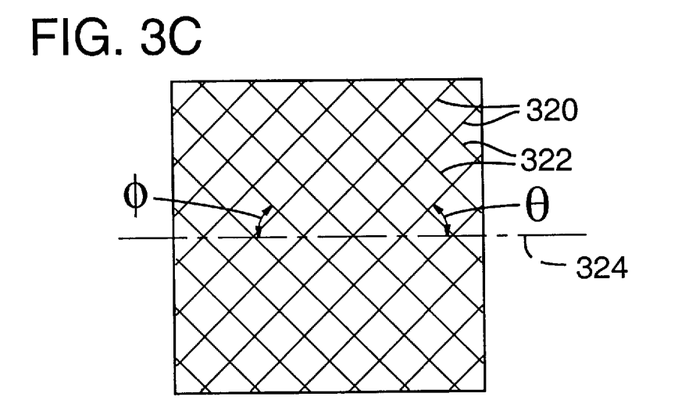

It will be apparent that other deformable patterns can be substituted for the deformable Amsler grid 104. Alternative patterns include grid patterns formed by unevenly spaced lines or by series of non-perpendicular lines, for example a triangular grid or a series of parallel curves. With reference to FIG. 3A, a series of concentric, preferably equally spaced circles 301 can be used to form a regular, repeating pattern in which the curves are equally spaced from one another, or are progressively spaced farther apart. Alternatively, the pattern can consist of a series of parallel, equally spaced lines 304 tilted from a horizontal axis 306, as shown in FIG. 3B. Another example of a grid pattern is shown in FIG. 3C, where the grid is formed by the intersection of two series of parallel lines 320, 322, tilted at different angles $\theta$, $\phi$, from a horizontal axis 324. The grid pattern shown in FIG. 2 could also be rotated so that the lines are tilted from horizontal and vertical. The preferred grid pattern will have straight lines, which more easily permit detection of metamorphopsia.

One or more straight lines scanned across the computer monitor 47 can also be used. Such a line is slowly scanned across the display screen with the subject's gaze fixed, for example at a central fixation point. When the subject notices a distortion, scanning stops and the subject is instructed to correct the line by moving various points on the line until the line appears straight. This manipulation causes the line to be offset slightly from its straight shape. Once the line appears straight after an offset is applied, the line is scanned again until it once more appears distorted. Alternatively, the line can be scanned across the display screen 106 while the subject's gaze is fixed, identifying areas in which distortions are observed. When this scan is complete, the line is moved to areas at which the subject reported distortions and the subject corrects these perceived distortions. After the line is distorted so that it is not perceived as curved at a location in the visual field, the deformations are recorded and the line moved to another location of perceived distortion.

Although in the preferred embodiment, the pattern generator uses a computer to generate the deformable grid pattern, patterns obtained in other ways are also suitable. For example, a deformable mechanical grid that is adjustable by physically moving elements of the grid can serve as the deformable pattern.

Computer input devices other than the mouse 42 of the preferred embodiment may also be used to distort the grid or other pattern. Representative devices include trackballs, joysticks keyboards, and touchpads. While a computer is convenient for recording the deformations of the deformable grid pattern by the subject, these deformations can be recorded manually as well.

The display presented to the subject can also be projected into the eye, or swept across the retina. The specific type of display is not essential to the method of the present invention.

EXAMPLE 6

The grid or other pattern of the present invention establishes a mathematical function that samples visual distortion, for example at the vertices of the grid. Intermediate values of distortion between sample points (e.g. between vertices of the grid) can be interpolated to provide a continuous mathematical function describing the metamorphopsia described by the subject. This information permits a variety of therapeutic interventions, such as the design of lenses, or the morphing of video images in accordance with the mathematical function. Using conventional computer morphing technology, portions of any image can be purposefully distorted in accordance with the mathematical function that defines the distortion, so that the image will be perceived by the subject with metamorphopsia as being substantially undistorted.

Because the distortions of metamorphopsia are generally stable, a compensating lens can be provided to correct these distortions. The compensating lens is preferably stabilized with respect to the retina. For example, a toric contact lens or an intraocular anterior chamber implant can be provided that compensates for the patient's particular distortions. Such lenses are stable in position and orientation with respect to the cornea and retina. Corrective lenses or filters can be designed to compensate for distortion, as shown for example in U.S. Pat. No. 5,308,991, which is incorporated by reference. The lens that is made will preferably distort a regular grid pattern to the image of the distorted grid mapped by the device of the present invention. A lens which causes such a distortion will neutralize the distortion perceived by the subject with metamorphopsia.

Alternatively, a digital or optical filter can be provided that is controlled by an eye-tracking system. A filter can also be provided that is fixed relative to a display screen. Correction of images on a computer display is readily implemented, so that a subject with metamorphopsia can view an image on a computer screen without perceiving distortion. After the distortions of the deformable pattern are measured, distortion as a function of position is known. Images to be presented to the subject on the screen are then predistorted so that they appear undistorted. An example of an apparatus for geometrical correction of a distorted video image is shown in U.S. Pat. No. 5,231,673, which is incorporated by reference. To maintain correction as the gaze of the subject deviates from fixation, an eye tracker can provide an output corresponding to the deviation from fixation, and the predistortion can account for this deviation. Alternatively, the subject can maintain fixation on a predetermined target to avoid misregistration with the corrected video image.

In view of the many possible embodiments to which the principles of the invention may be applied, it should be recognized that the illustrated embodiment is only a preferred example of the invention and should not be taken as a limitation on the scope of the invention. Rather, the scope of the invention is defined by the following claims. I therefore claim as my invention all that comes within the scope and spirit of these claims.

I claim:

1. An apparatus for evaluating metamorphopsia in a subject, the apparatus comprising:
   a display that displays a line pattern suitable for detecting metamorphopsia as a distortion in the line pattern;
   a visual fixation target associated with the line pattern; and
   an input device that selectively deforms portions of the line pattern that appear distorted to the subject, to provide a deformed pattern that neutralizes the distortion perceived by the subject.

2. The apparatus of claim 1 further comprising a recorder for recording the selectively deformed pattern.

3. The apparatus of claim 1 further comprising a pattern generator for generating the line pattern.

4. The apparatus of claim 3, wherein the line pattern comprises a grid.

5. The apparatus of claim 1 further comprising a marker for demarcating an area of scotoma on the line pattern.

6. The apparatus of claim 5 wherein the fixation target is substantially at a center of the pattern.

7. The apparatus of claim 5 wherein the marker comprises a cursor, movable with respect to the deformable pattern, which marks areas of scotoma on the pattern.

8. The apparatus of claim 1, wherein the pattern comprises a series of orthogonal lines.

9. The apparatus of claim 8, wherein the orthogonal lines are substantially equally spaced.

10. The apparatus of claim 9 wherein the orthogonal lines are substantially horizontal and vertical.

11. The apparatus of claim 9 wherein the pattern comprises an Amsler grid.

12. The apparatus of claim 1 wherein the pattern comprises orthogonal lines that intersect at a plurality of vertices, and the pattern is deformed by moving one or more of the vertices.

13. A method of evaluating metamorphopsia comprising:
    displaying a regular pattern of substantially equally spaced lines that intersect at multiple vertices, wherein the pattern is suitable for detecting metamorphopsia in a subject as a distortion in the pattern;
    selectively deforming the pattern to substantially neutralize the distortion perceived by the subject by moving one or more of the vertices.

14. The method of claim 13 further comprising displaying a visual field deficit marker at selected positions in the pattern, and marking areas of the pattern in which the marker is not perceived by the subject.

15. The method of claim 14 wherein displaying the pattern comprises displaying a series of orthogonal lines.

16. The method of claim 15 further comprising displaying a fixation target in the pattern.

17. The method of claim 13 wherein displaying a regular pattern comprises displaying a series of parallel lines or curves.

18. The method of claim 13, wherein displaying the pattern comprises displaying a grid pattern in which lines intersect at multiple vertices, and selectively deforming the pattern comprises moving one or more of the vertices until that distortion is substantially neutralized.

19. The method of claim 13 further comprising recording the selectively deformed pattern.

20. The method of claim 19, wherein recording the selectively deformed pattern comprises recording the magnitude and direction of a displacement of each of the vertices from an original position of the vertex in the pattern.

21. The method of claim 13, further comprising using the selectively deformed pattern to distort a separate image to neutralize a distortion of the separate image.

22. The method of claim 21, wherein the method is a computer assisted method, the grid pattern is displayed on a computer screen, and the grid pattern and areas are stored in computer memory.

23. A computer readable medium that includes the steps of claim 13.

24. The method of claim 13, further comprising using distortion of the selectively deformed pattern to distort a subsequent image perceived by the subject by interpolating distortion within the pattern, and distorting the subsequent image in accordance with the interpolated distortion within the pattern.

25. A method of measuring metamorphopsia in a subject, comprising:
    providing a deformable grid pattern comprising an intersecting series of orthogonal, substantially equally spaced lines that intersect at a plurality of vertices to form a grid, and a central fixation marker in the grid pattern for establishing visual fixation;
    moving a cursor throughout the grid pattern, while the subject maintains visual fixation on the fixation marker, and marking one or more areas of scotoma in the pattern where the cursor is not visible to the subject;

deforming the grid pattern by displacing one or more of the vertices to neutralize the distortion until the deformable grid pattern appears substantially regular to the subject, whereby a deformed grid pattern is formed; and storing the deformed grid pattern and marked areas of scotoma in the pattern where the cursor is not visible to the subject.

26. An computer system for measuring metamorphopsia in a subject, comprising:

a pattern generator for generating a deformable grid pattern on a display screen, the pattern having a fixation target and substantially equally spaced, orthogonal lines that intersect at a plurality of vertices;

a cursor that is movable throughout the pattern;

an input device that marks areas of the pattern where the cursor is not visible to the subject, and displaces one or more vertices of the intersecting lines from an original vertex position, in response to input from the subject, thereby forming a deformed grid pattern which neutralizes the metamorphopsia seen by the subject; and a memory device that stores the areas of the pattern where the cursor is not visible to the subject, and records displacements of the vertices from the original position.

27. The computer system of claim 26, wherein the input devices marks areas of the pattern where the cursor is not visible to the subject with a colored spot.

28. The method of claim 27, wherein the subsequent image is distorted digitally or optically.

* * * * *

UNITED STATES PATENT AND TRADEMARK OFFICE
CERTIFICATE OF CORRECTION

PATENT NO. : 5,892,570
DATED : April 6, 1999
INVENTOR(S) : Kent A. Stevens

It is certified that error appears in the above-indentified patent and that said Letters Patent is hereby corrected as shown below:

In Column 7/Line 11, change "generator 103" to --generator to--.

In Column 11/Line 31, change "an output" to --an input--.

Signed and Sealed this

Twentieth Day of March, 2001

Attest:

NICHOLAS P. GODICI

*Attesting Officer*  *Acting Director of the United States Patent and Trademark Office*